US00PP09582P

United States Patent [19]

Meilland

[11] Patent Number: Plant 9,582

[45] Date of Patent: Jun. 18, 1996

[54] HYBRID TEA ROSE PLANT NAMED 'MEIREVOLT'

[75] Inventor: Alain M. Meilland, Antibes, France

[73] Assignee: The Conard-Pyle Company, West Grove, Pa.

[21] Appl. No.: 496,161

[22] Filed: Jun. 28, 1995

[51] Int. Cl.[6] ..... A01H 5/00

[52] U.S. Cl. ..... Plt./15

[58] Field of Search ..... Plt./15, 24

*Primary Examiner*—Howard J. Locker

*Attorney, Agent, or Firm*—Burns, Doane, Swecker & Mathis

[57] ABSTRACT

A new and distinct variety of Hybrid Tea rose plant is provided which abundantly forms on a substantially continuous basis attractive very double yellow blossoms. Such blossoms are long-lasting and exhibit good petal-drop characteristics. The plant exhibits attractive dark green glossy foliage, vigorous somewhat compact vegetation, and very good disease resistance. The new variety is particularly well suited for growing as attractive ornamentation in the outdoor landscape, such as in parks and gardens.

1 Drawing Sheet

SUMMARY OF THE INVENTION

The new variety of Hybrid Tea rose plant was created by artificial pollination wherein two parents were crossed which previously had been studied in the hope that they would contribute the desired characteristics. The female parent (i.e., the seed parent) of the new variety was the 'Meinuzeten' variety U.S. Plant Pat. No. 4,224). The male parent (i.e., the pollen parent) was the product of the pollination of the 'King's Ransom' variety (U.S. Plant Pat. No. 2,103) and the 'Landora' variety (non-patented in the United States). The 'Meinuzeten' variety is being marketed under the Ambassador trademark. The 'Landora' variety sometimes is known as the 'Sunblest' variety. The parentage of the new variety can be summarized as follows:

'Meinuzeten'×('King's Ransom'×'Landora').

The seeds resulting from the above pollination were sown and small plants were obtained which were physically and biologically different from each other. Selective study resulted in the identification of a single plant of the new variety.

It was found that the new variety of Hybrid Tea rose plant of the present invention possesses the following combination of characteristics:

(a) forms attractive very double yellow blossoms in abundance on a substantially continuous basis,
(b) forms attractive dark green glossy foliage,
(c) exhibits a vigorous growth habit,
(d) exhibits very good disease resistance, and
(e) is particularly well suited for growing as attractive ornamentation in the landscape.

The new variety well meets the needs of the horticultural industry and is particularly well adapted for decorating the outdoor landscape in parks and gardens.

The new variety has been found to undergo asexual propagation in France by a number of routes, including budding, grafting, and cuttage. Asexual propagation by the above-mentioned techniques in France has shown that the characteristics of the new variety are stable and are strictly transmissible by such asexual propagation from one generation to another.

The new variety has been named the 'Meirevolt' variety.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety were two years of age and were observed during June while budded on *Rosa froebelli* understock and growing outdoors at Le Cannet des Maures, Var, France.

FIG. 1—illustrates a specimen of a young shoot,

FIG. 2—illustrates a specimen of a floral bud before the opening of the sepals;

FIG. 3—illustrates a specimen of a floral bud at the opening of the sepals;

FIG. 4—illustrates a specimen of a floral bud at the opening of the petals;

FIG. 5—illustrates a specimen of a flower in the course of opening;

FIG. 6—illustrates a specimen of an open flower — plan view — reverse;

FIG. 7—illustrates a specimen of an open flower — plan view — obverse;

FIG. 8—illustrates a specimen of a fully open flower — plan view — obverse;

FIG. 9—illustrates a specimen of a floral receptacle showing the arrangement of the stamens and pistils;

FIG. 10—illustrates a specimen of a floral receptacle showing the arrangement of the pistils (stamens removed);

FIG. 11—illustrates a specimen of a flowering stem;

FIG. 12—illustrates a specimen of a main branch;

FIG. 13—illustrates specimens of a two leaves with three leaflets each — plan view — upper surface (top) and under surface (bottom); and FIG. 14—illustrates specimens of two leaves with five leaflets each — plan view — under surface (top) and upper (bottom).

DETAILED DESCRIPTION

Figures 1, 2, 3, 4, 5, 6, 7, 8, 9, 10, 11, 12, 13, 14:
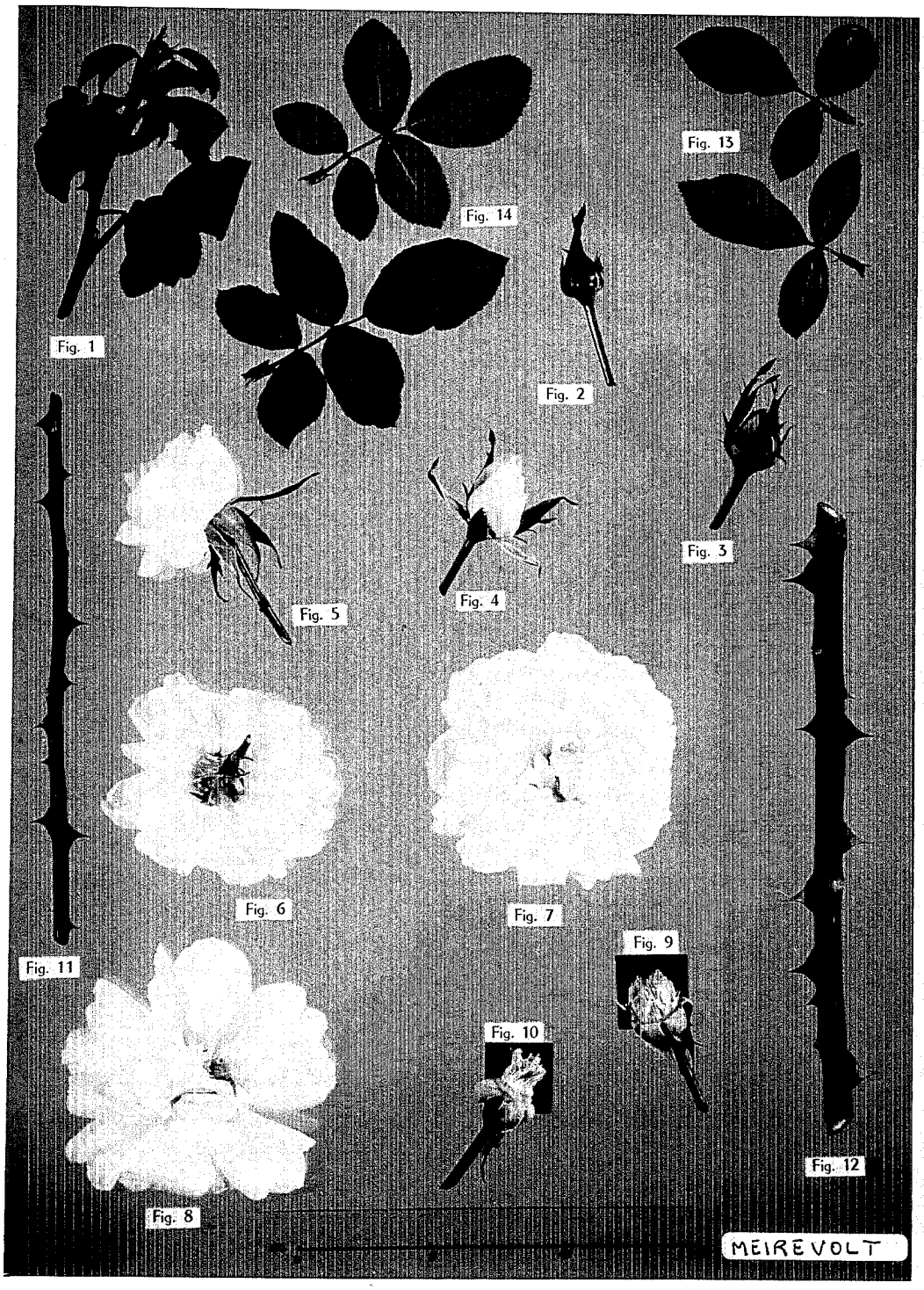

The chart used in the identification of the colors is that of the Royal Horticultural Society (R.H.S. Colour Chart). The description is based on the observation of the two year-old plants observed during June while budded on *Rosa froebelli* understock and growing outdoors at Le Cannet des Maures, Var, France. The coloration in common terms precedes reference to the chart.

Class: Hybrid Tea.

Plant:

*Height.*—Approximately 70 to 80 cm. on average at the end of the growing season. Stem lengths of approximately 20 to 40 cm. commonly are produced on a mature bush.

*Habit.*—Bushy.

Branches:

*Color.*—Young stems: Yellow-Green Group 146B and more or less maculated with reddish coloration. Adult wood: medium green, Green Group 143B.

*Thorns.*—Size: medium. Quantity: moderately numerous to numerous. Color: pinkish on young stems and greenish on adult wood.

Leaves:

*Stipules.*—Adnate, pectinate, and moderately wide and linear.

Petioles.—Upper surface: striped reddish on young foliage and medium green on adult foliage with more or less glandular edges. Under surface: light green, and bear some small thorns.

Leaflets.—Number: 3, 5 (most often), and 7. Shape: elliptic. Serration: simple and regular. Texture: leathery. General appearance: dense, and glossy foliage. Color (young foliage): upper surface: Yellow-Green Group 146B, and more or less maculated with reddish coloration. under surface: Yellow-Green Group 146B, and more or less maculated with reddish coloration. Color (adult foliage): upper surface: dark green, Green Group 137A. under surface: light green, Green Group 137C.

Inflorescence:

*Number of flowers.*—Usually one per stem, and sometimes up to approximately 3 flowers per stem. The flowers productivity is good and generally is typical for a variety of this class.

*Peduncle.*—Light green and smooth. The length is approximately 2 to 3 cm. on average.

Sepals.—Upper surface: tomentose, and light green in coloration on both surfaces (as illustrated). Under surface: light green with a few glandular and appendiculated edges.

*Buds.*—Shape: globular. Length: approximately 2.5 to 3 cm. on average. Size: large. Color upon opening: upper surface: Aureolin Yellow, Yellow Group 12A. A slight greenish coloration commonly initially is present. Under surface: Straw Yellow, Yellow Group 13C. A slight greenish coloration commonly initially is present.

*Flower.*—Shape: Cupped. Diameter: approximately 9 to 10 cm. on average. Color (when opening begins): upper surface: Aureolin Yellow, Yellow Group 12A. under surface: Straw Yellow, Yellow Group 13C. Color (when blooming): upper surface: Aureolin Yellow, Yellow Group 12A. under surface: Straw Yellow, Yellow Group 13C. Color (at end of opening): upper surface: Aureolin Yellow, Yellow Group 12A. under surface: Straw Yellow, Yellow Group 13C. Fragrance: none. Lasting quality: very long. The lasting quality of the blossoms varies with the weather conditions that are encountered. For instance, under generally normal growing conditions the blossoms commonly last approximately 10 to 12 days when present on the plant, and approximately 7 days when cut and placed in a vase. Petal form: oval and cuneiform, very thin at midflower, and with reflexed edges. Petal drop: good. The petals tend to drop cleanly when fully mature in the absence of undue clinging. Stamen number: approximately 35 on average. Petal number: approximately 87 to 90 on average. Petal shape: typically exhibit an oval tip and a wedge-shaped base. Anthers: commonly located below the stigmas, and normal golden yellow edged with ochre in coloration. Filaments: bright yellow in coloration. Pistils: approximately 70 on average. Stigmas: normal strawlike in coloration. Styles: tomentose at base, greenish straw in coloration, and sometimes exhibit a vegetative center. Receptacle: medium green, smooth, and in longitudinal section in the shape of a funnel. Hips: none observed to date.

Development:

*Vegetation.*—Vigorous and somewhat compact.

*Blooming.*—Very abundant on a substantially continuous basis.

*Resistance to diseases.*—very good.

I claim:

1. A new and distinct variety of Hybrid Tea rose plant characterized by the following combination of characteristics:

(a) forms attractive very double yellow blossoms in abundance on a substantially continuous basis,
(b) forms attractive dark green glossy foliage,
(c) exhibits a vigorous growth habit,
(d) exhibits very good disease resistance, and
(e) is particularly well suited for growing as attractive ornamentation in the landscape, substantially as herein shown and described, and the parts thereof.

* * * * *

MEIREVOLT